United States Patent
Koppe et al.

(10) Patent No.: US 6,442,235 B2
(45) Date of Patent: Aug. 27, 2002

(54) METHOD OF IMAGING THE BLOOD FLOW AS A FUNCTION OF TIME IN AN OBJECT TO BE EXAMINED

(75) Inventors: Reiner Heinrich Koppe, Hamburg; Erhard Paul Artur Klotz, Neumünster; Michael Harald Kuhn, Hamburg, all of (DE); John Op De Beek, Eindhoven (NL)

(73) Assignee: Koninkijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/749,147

(22) Filed: Dec. 27, 2000

(30) Foreign Application Priority Data

Jan. 5, 2000 (DE) .......................................... 100 00 185

(51) Int. Cl.⁷ .............................................. G01N 23/24
(52) U.S. Cl. .................................. 378/62; 378/4; 378/8
(58) Field of Search ............................ 378/62, 8, 4, 41

(56) References Cited

U.S. PATENT DOCUMENTS

| | | | | |
|---|---|---|---|---|
| 4,853,947 A | * | 8/1989 | Haaker et al. | 378/99 |
| 4,888,794 A | * | 12/1989 | Haaker et al. | 378/41 |
| 5,852,646 A | * | 12/1998 | Klotz et al. | 378/8 |
| 5,978,439 A | * | 11/1999 | Koppe et al. | 378/8 |

\* cited by examiner

Primary Examiner—Robert H. Kim
Assistant Examiner—Irakli Kiknadze
(74) Attorney, Agent, or Firm—John Vodopia

(57) ABSTRACT

The invention relates to a method of imaging the blood flow as a function of time in an object (3) to be examined, which method includes the following steps:
a) acquisition of a series of X-ray projection images ($D_i$; $E_j$) during administration of a contrast medium to the blood vessels in the object (3) to be examined,
b) acquisition of an image data set (H; K) containing the course of the blood vessels in the object (3) to be examined,
c) segmentation of the regions of the blood vessels in the individual X-ray projection images ($D_i$; $E_j$) that are filled with contrast medium,
d) encoding the image data set (H; K) in time by comparing the image data set (H; K) with the segmented X-ray projection images ($D_j'$; $F_j$), and
e) displaying one or more images (B) formed from the time-encoded image data set (H'; R') and representing the blood flow as a function of time.

Figure 1:
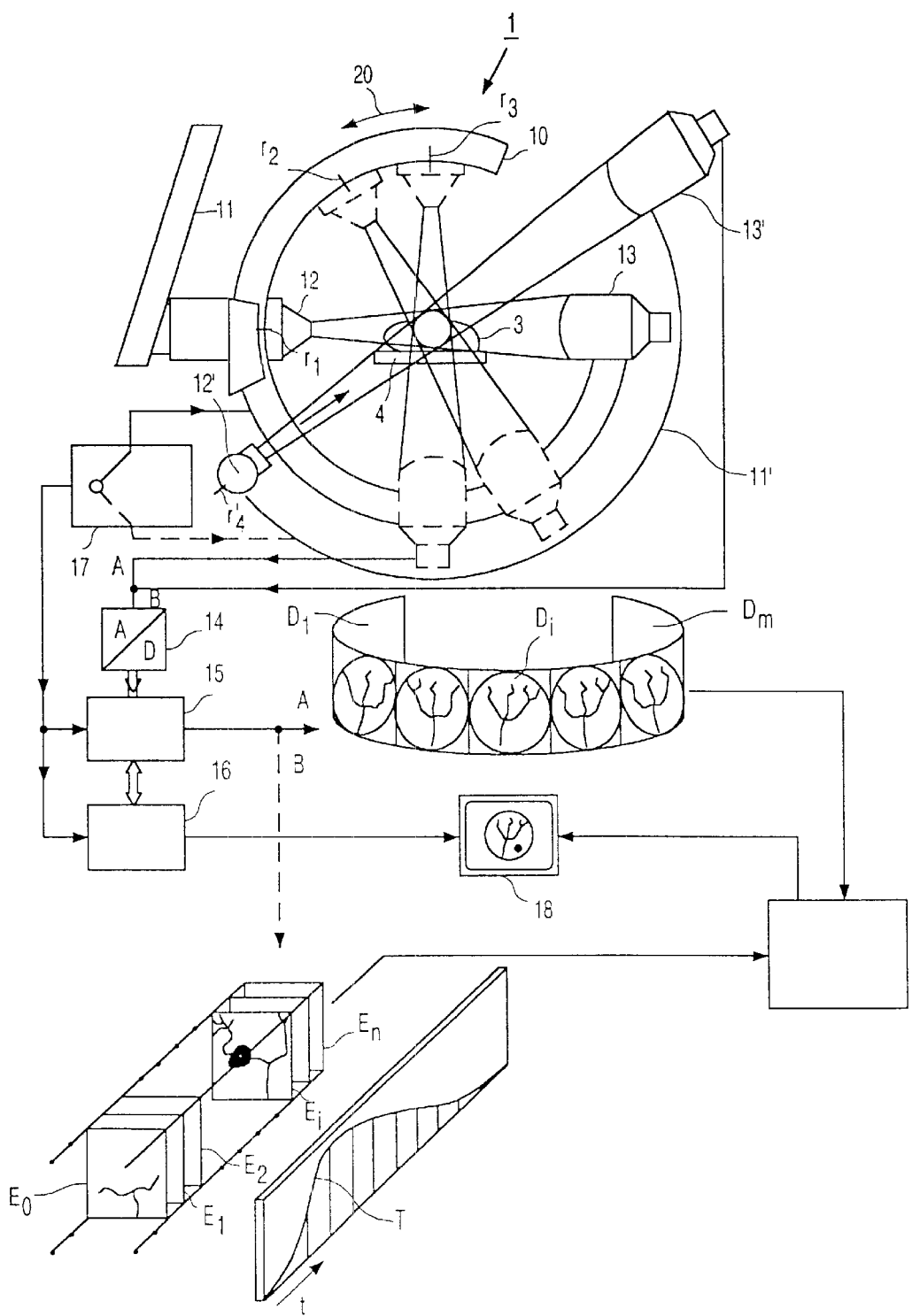

The invention also relates to a correspondingly constructed X-ray device.

11 Claims, 5 Drawing Sheets

METHOD OF IMAGING THE BLOOD FLOW AS A FUNCTION OF TIME IN AN OBJECT TO BE EXAMINED

The invention relates to a method of imaging the blood flow as a function of time in an object to be examined, as well as to an X-ray device for carrying out this method.

EP 860 696 A2 discloses a method which enables the reproduction of distributed structures, for example a vascular system filled with a contrast medium, in a synthetic projection image which reproduces the parts of the vascular system that are present in a selectable sub-volume more clearly than the X-ray images that are acquired from different perspectives and wherefrom this projection image is derived. This method thus yields a time-averaged "frozen" image of the vascular system in which the blood flow as a function of time is not visible.

Three-dimensional rotation angiography produces a series of X-ray projection images of the object to be examined from different projection directions while a contrast medium is injected into the blood vessels of the object to be examined. Using a known reconstruction algorithm, for example the Feldkamp algorithm, a three-dimensional image is derived from such X-ray projection images; this three-dimensional image reproduces the vascular system in space in a time-averaged manner. In two-dimensional angiography it is also known to form a two-dimensional "frozen" image of the vascular system.

For various applications, such as the analysis of pathologies of the cerebral vessels, for example in the case of vascular anomalies (stenoses, arteriovenous deformations), however, it is important to know and reproduce the blood flow as a function of time. Therefore, it is an object of the invention to provide a method which enables the reproduction of the blood flow in an object to be examined as a function of time, and to provide an appropriate X-ray device for carrying out this method.

Such a method should also take into account the fact that a contrast medium cannot be repeatedly injected into the same patient within a short period of time, so that the method should do, if at all possible, with a single contrast medium injection. Moreover, it should be possible to acquire the images in an as short as possible period of time, at an as small as possible expenditure and with an as high as possible resolution.

This object is achieved by means of the method disclosed in claim 1 and the X-ray device disclosed in claim 10.

The invention is based on the recognition of the fact that an image data set, which may be a two-dimensional or a three-dimensional image data set and contains information concerning the course of the blood vessels in the object to be examined, can be encoded in time in such a manner that it also contains information concerning the blood flow as a function of time. Such encoding in time is performed according to the invention in that the image data set is compared with a series of X-ray projection images; these X-ray projection images are formed successively in time and contain the information concerning the distribution of an injected contrast medium in the blood vessels at each time a different instant. Because each X-ray projection image is individually compared with the image data set, that is, each image value of the image data set is compared with the image values of the individual X-ray projection images, it is quasi checked which parts of the vascular system contained in the image data set are filled with the contrast medium at the individual instants associated with the respective X-ray projection images. Using suitable reproduction methods, the image data set thus encoded in time can be converted into one or more images which show the blood flow as a function of time.

The version disclosed in claim 2 is particularly suitable for two-dimensional rotation angiography. It already offers a two-dimensional X-ray image data set, for example a two-dimensional X-ray projection image which completely contains the vascular system filled with contrast medium and may be a previously formed or an instantaneous X-ray image data set. The actual X-ray projection images derived from a fixed X-ray position during a contrast medium administration are subtracted from one another in conformity with this version, so that each difference image contains the information as regards the path followed by the contrast medium in the vascular system between the two instants at which the two subtracted X-ray projection images were acquired. Such difference images are then used for the time encoding of the X-ray image data set.

A further version of this method is disclosed in claim 3. This version represents a simple possibility for comparing the image data set with the difference images. In order to enhance the imaging precision, first an X-ray image data sub-set is segmented from the X-ray image data set; this sub-set contains only the information concerning the course of the blood vessels. Subsequently, for each difference image there is acquired an associated pixel sub-set in such a manner that the pixels of the individual difference images are compared with the pixels of the X-ray image data sub-set and that with each pixel sub-set there are associated those pixels of the X-ray image data sub-set for which the associated difference image includes corresponding pixels. Each pixel sub-set thus contains the information concerning the distribution of the contrast medium at a given instant and one or more projection images which show the blood flow as a function of time can be derived from the pixel sub-sets.

According to the preferred version disclosed in claim 4, the X-ray projection images are acquired from different positions. The image data set then constitutes a three-dimensional X-ray image data set derived from such X-ray projection images. Thus, according to this further version only a single series of X-ray projection images is acquired from different directions, said images also containing the time information. After segmentation of the blood vessels in said X-ray projection images they are compared with the X-ray image data set and encoded in time, for example, in that pseudo-projection images are calculated from the X-ray image data set, utilizing the known imaging geometry of the X-ray device, so as to be compared with the actual X-ray projection images.

Claim 5 discloses a particularly attractive further version which is also suitable for three-dimensional rotation angiography. Two series of X-ray projection images are acquired therein, the first series being acquired from a fixed X-ray position whereas the second series is acquired from different X-ray positions. This operation can be performed either successively in time, be it that two contrast medium injections are then required, or simultaneously by means of an X-ray device which includes two imaging units. From the X-ray projection images of the first series there are derived difference images which, as described above, contain the time information whereas a three-dimensional X-ray image data set is acquired from the X-ray projection images of the first series by means of a known reconstruction algorithm. This X-ray image data set is encoded in time by means of the difference images. This further version, notably the formation of difference images as carriers of the time information, offers the advantage that the difference images always contain only the variation in time of the contrast medium flow (=the blood flow) in a given time interval whereas in the case of direct use of the X-ray projection images as carriers of the time information the overall distribution of the contrast medium in the vascular system is always contained therein and hence the information is significantly less exact. This is also due to the fact that the contrast medium propagates very quickly throughout the vascular system to be observed, so that the differences in the distribution of the contrast medium between two comparatively closely spaced instants are only comparatively small.

The claims 6 and 7 disclose preferred possibilities for the time encoding of the image data set and the comparison of the image data set with the segmented X-ray projection images. The steps of the method as disclosed in claim 7 correspond to the method which is known from EP 880 109 A2 whose disclosure is explicitly referred to herein and is considered to be incorporated herein. The latter publication describes a method of determining the spatial transformation between a three-dimensional object reproduced by a data set and the object itself. A pseudo-projection image is then calculated for a part of the volume reproduced by the data set; this pseudo-projection image is compared with an X-ray projection image of the object itself. The parameters on which the calculation of the pseudo-projection image is based are then varied until an optimum match is obtained. This method can be advantageously used in an appropriate manner in conjunction with the present invention.

The claims 8 and 9 disclose advantageous further versions concerning the display of the blood flow as a function of time. For example, the time information can be converted into a color code so that the complete two-dimensional or three-dimensional data set can be reproduced as an image with the corresponding color code. The encoded pixel subsets or voxel sub-sets can also be reproduced successively in time, for example as an endless loop, thus creating the impression of blood flowing through the blood vessels. It is also feasible to enable reproductions from arbitrary angles of observation and rotation of the image is also possible.

An X-ray device which is suitable for carrying out the method according to the invention is disclosed in claim 10; as is indicated in the embodiment of claim 11, it may also include a second imaging unit.

Figure 2:
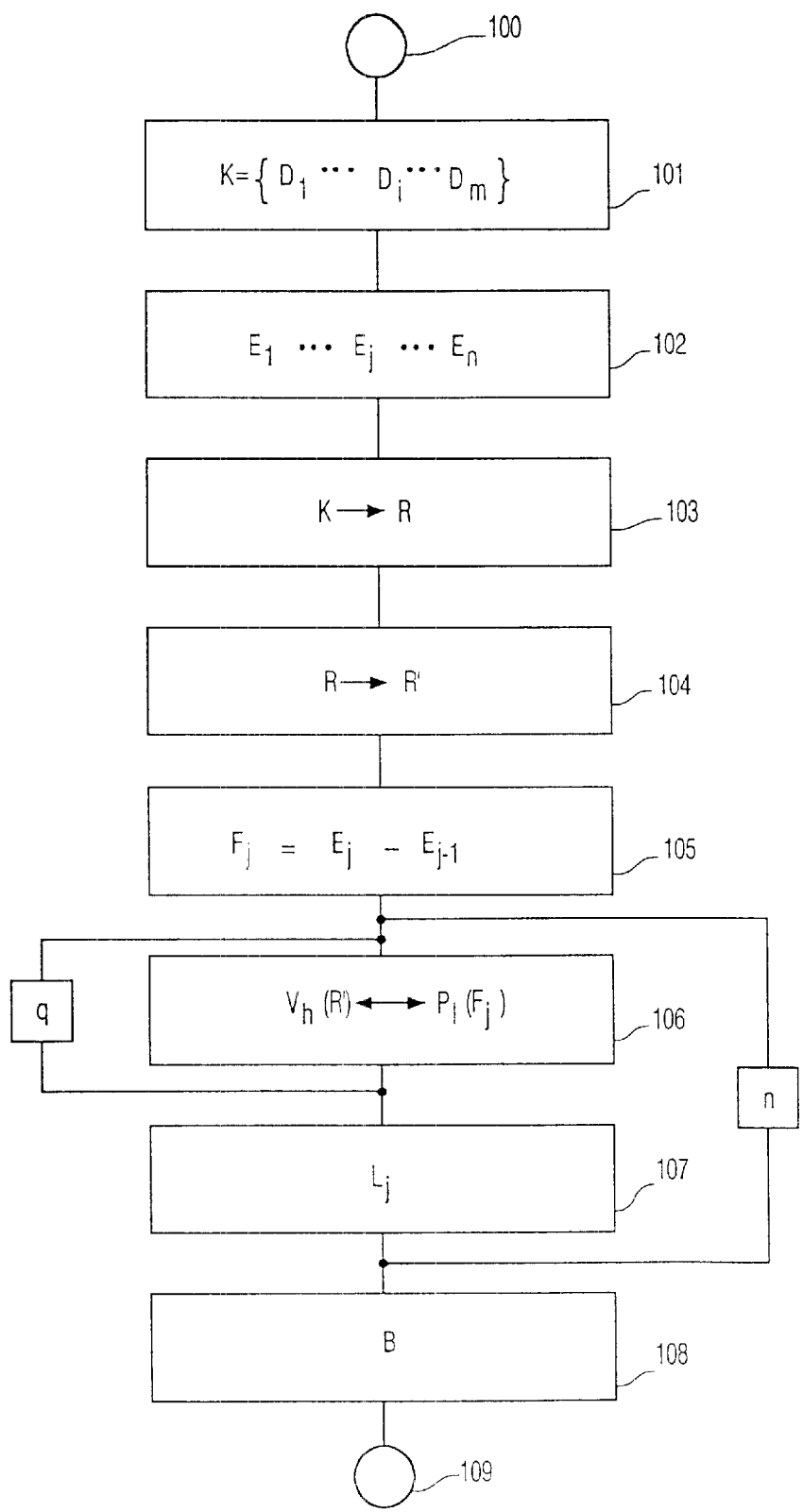
Figure 3:
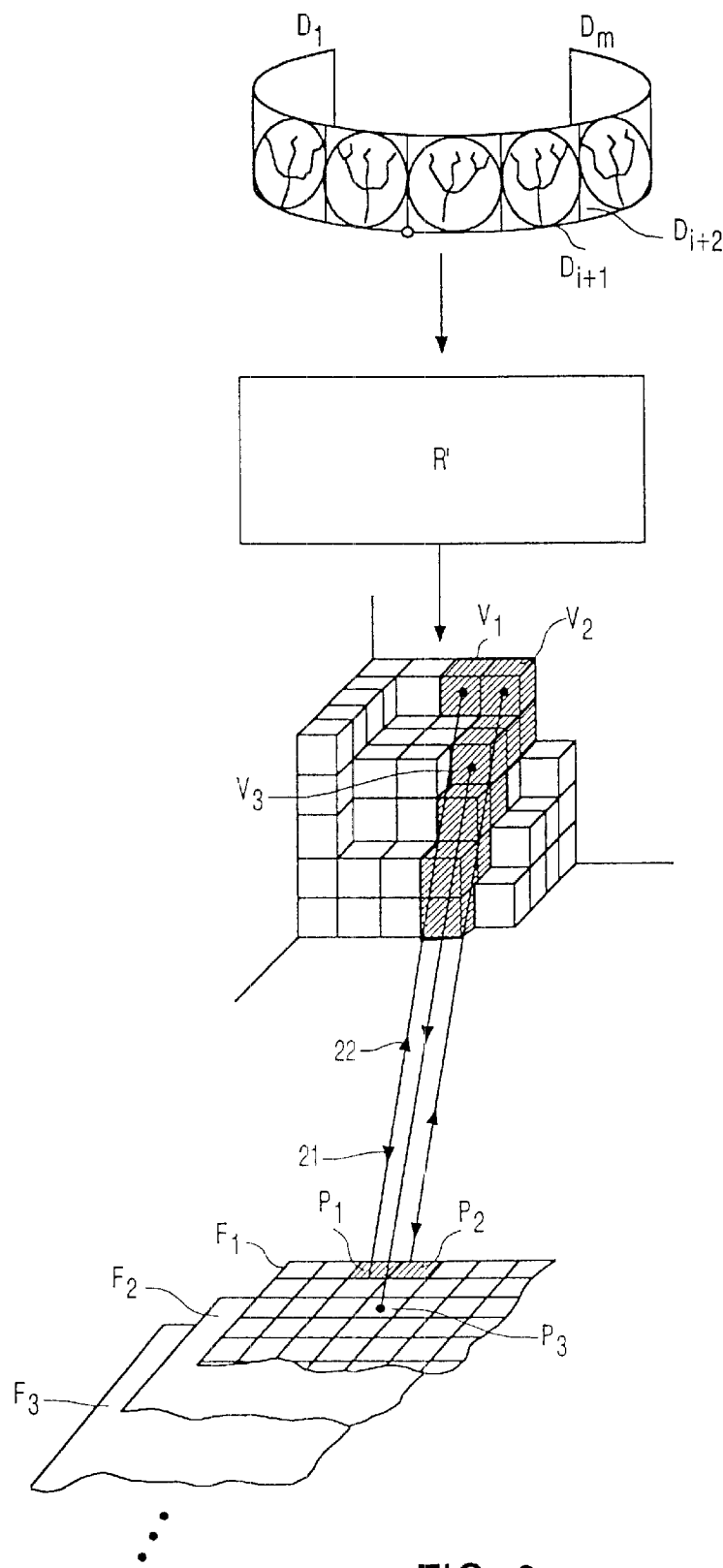
Figure 4:
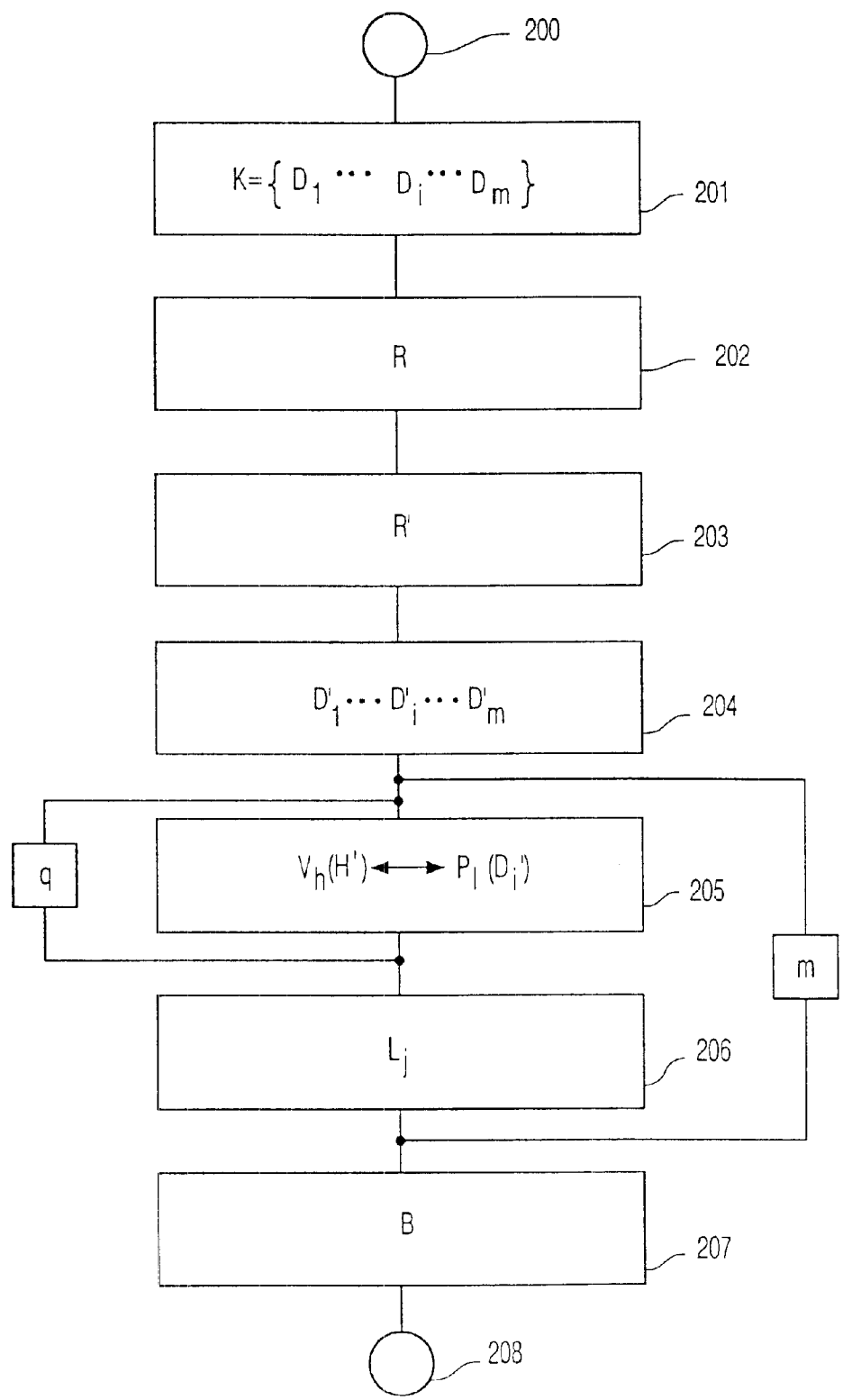
Figure 5:
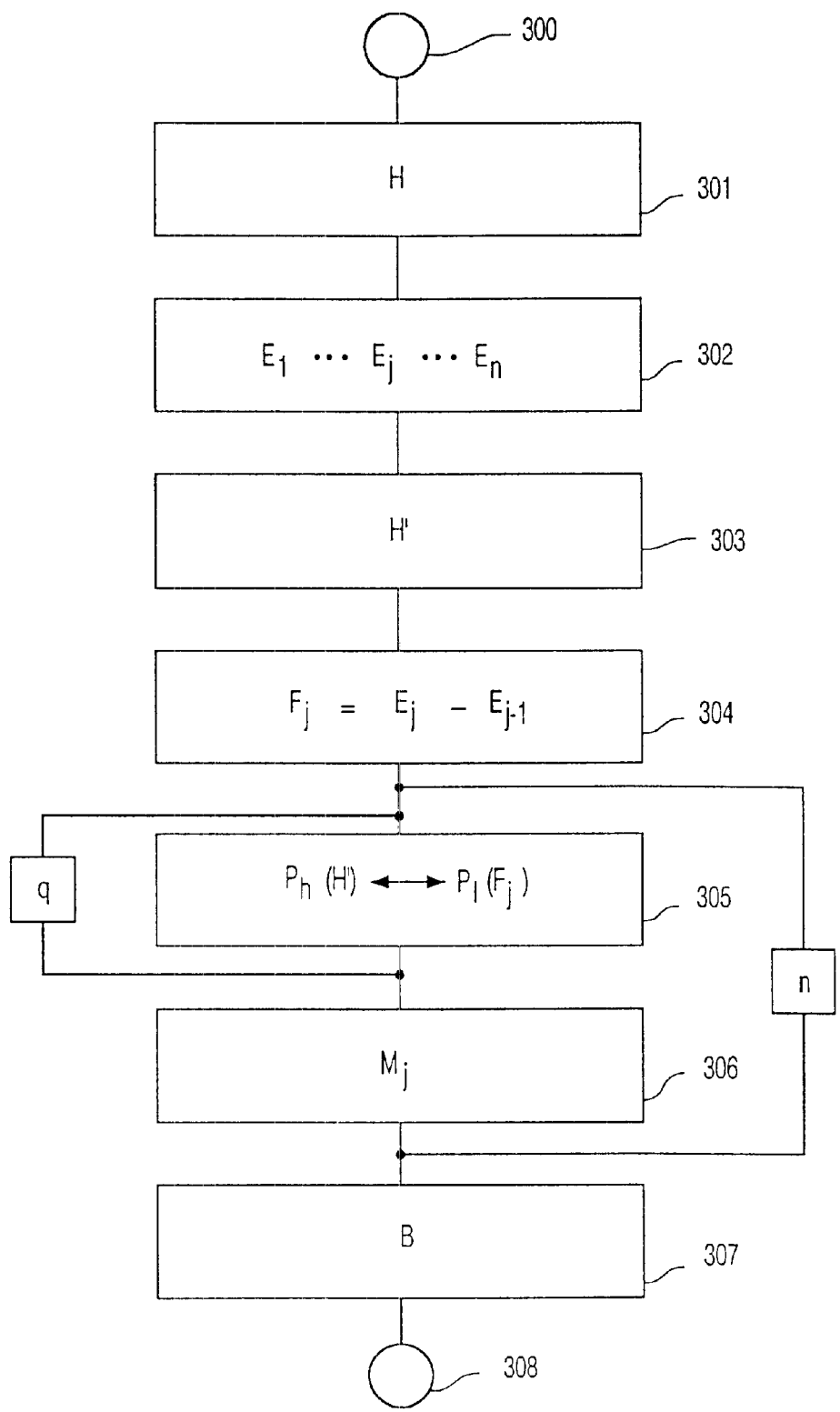

The invention will be described in detail hereinafter with reference to the drawings. Therein:

FIG. 1 shows an X-ray device for carrying out the method according to the invention, FIG. 2 shows a flow chart illustrating a first version of the method according to the invention, FIG. 3 illustrates diagrammatically the encoding in time, FIG. 4 shows a flow chart of a second version of the method according to the invention, and FIG. 5 shows a flow chart of a third version of the method according to the invention.

FIG. 1 shows an X-ray device 1 which serves to form two-dimensional X-ray images of an object 3 to be examined, for example, a patient who is arranged on a table 4. The X-ray device 1 includes an X-ray source 12 and an X-ray detector 13 which are aligned relative to one another and mounted on a C-arm 10 which itself is journalized in a stand 11 which is only partly shown. The C-arm 10 can be pivoted about a perpendicular axis on the one hand and be rotated around its center in the direction of the double arrow 20 on the other hand, for example through 180°, by means of a motor drive (not shown). During this motion a plurality of X-ray images can be acquired so as to image the object 3 to be examined from different, reproducible perspectives or X-ray positions $r_1, r_2, r_3$ of the imaging unit 12, 13. Also provided are a second X-ray source 12' and a second X-ray detector 13' which are mounted on a supporting device 11' and are capable of forming X-ray images of the object 3 to be examined from a fixed X-ray position $r_4$.

Each of the X-ray detectors 13, 13' may be formed by a respective X-ray image intensifier whereto there is connected a television chain whose output signals are digitized by an analog-to-digital converter 14 so as to be stored in a memory 15. The X-ray projection images $D_1, \ldots D_i, \ldots D_{im}$, acquired by the imaging unit 12, 13 from different X-ray positions $r_1, \ldots r_i, \ldots r_m$ (of which only the positions $r_1, r_2, r_3$ are explicitly shown in the drawing), can be processed by an image processing unit 16 so as to be reproduced on a monitor 18 either individually or as a series of images. The X-ray projection images $E_0, E_1, E_2, \ldots, E_n$, acquired by the imaging unit 12', 13' from the fixed X-ray position r' at discrete instants t during a contrast medium bolus T, can also be processed by the image processing unit 16 so as to be displayed on the monitor 18. The individual components of the X-ray device are controlled by means of a control unit 17.

Also provided is an arithmetic unit 19 which receives the X-ray projection images $D_i$ and $E_j$ in order to derive therefrom images showing the variation in time of the blood flow in the relevant vessels of the object 3 to be examined. These images can be displayed on the monitor 18 again.

The invention will be illustrated hereinafter on the basis of the flow chart of a first version of the method according to the invention which is shown in FIG. 2. After the initialization (step 100) and after a contrast medium injection, the C-arm 10 is step-wise rotated about its center and at the same time a series of m X-ray projection images $D_i$ (for example, m=100) is formed, which projection images represent the object 3 to be examined and the blood vessels that are present therein and are filled with a contrast medium, from different perspectives (step 101). The X-ray projection images $D_i$ constitute a three-dimensional X-ray image data set K.

During a step 102 which takes place at the same time or at a later instant (after a further contrast medium injection), the imaging unit 12', 13' acquires a second series of X-ray projection images $E_j$ from a fixed perspective. During the subsequent step 103 on the one hand correction is made for imaging errors which are due, for example, to the imperfection of the imaging device or to the mechanical deformation of the C-arm. On the other hand a three-dimensional reconstruction image R is formed from the X-ray projection images $D_i$ by means of a known reconstruction algorithm. In the step 104 a reconstruction sub-image R' is formed from said reconstruction image R, which reconstruction sub-image contains, mainly or exclusively, information concerning the course of the blood vessels in the region examined. This reconstruction sub-image R' contains q voxels $V_k$ which are characterized by their co-ordinates in space.

During a further step 105 respective difference images $F_j$ are determined from each time two successively acquired X-ray projection images $E_{j-1}$ and $E_j$; such difference images contain only the information concerning the path traveled by the contrast medium in the period of time elapsing between the formation of the two X-ray projection images $E_{j-1}$ and $E_j$.

Subsequently, each of the n difference images $F_j$ is compared with the reconstruction sub-image R', so that the latter is encoded in time. To this end, in the step 106 each of the q voxels $V_k$ of the reconstruction sub-image R' is projected onto each difference image $F_j$, that is, a pseudo-projection image is calculated from the reconstruction sub-image R' so as to be compared with the individual difference images $F_j$. For the calculation of this pseudo-projection image it is necessary to know the geometry of the imaging unit 12', 13' in order to ensure that the co-ordinate system of the pseudo-projection image corresponds to the co-ordinate system of the X-ray projection images $E_j$ and the difference images $F_j$.

Due to the comparison of the voxels $V_k$ of the reconstruction sub-image R', or the pixels of the pseudo-projection image, with the pixels $P_1$ of the individual difference images $F_j$, the voxels of the reconstruction sub-image R' for which the corresponding difference image $F_j$ comprises a corresponding pixel are marked each time. The marked voxels are combined so as to form a voxel sub-set $L_j$ in the step 107.

In simplified form it may be stated that in the steps 106 and 107 it is checked to what segment of the vascular system the contrast medium has progressed in a time interval between the formation of two X-ray projection images $E_{j-1}$ and $E_j$, or from what segment of the vascular system the contrast medium has drained during this time interval, and that the voxels in the reconstruction sub-image R' which represent the relevant vessel segment are marked accordingly and combined so as to form a voxel sub-set $L_j$. These steps are carried out n times, that is, once for every difference image $F_j$. This results in n voxel sub-sets $L_j$ wherefrom one or more images B can be formed in the step 108, said images representing the blood flow as a function of time. For example, the voxels of each voxel sub-set $L_j$ can be reproduced in a different color in an overall image. The method is terminated in the step 109.

Notably the step 106 will be illustrated again with reference to FIG. 3. After a reconstruction sub-image R' has been determined from the X-ray projection images $D_i$ in several steps (which sub-image contains only the information concerning the vascular structure), the pixels $V_k$ of this reconstruction sub-image R' are projected onto the difference images $F_j$. Upon projection onto the first difference image Fl, the voxel $V_1$ along the projection ray 21 is projected onto the pixel $P_1$. On the basis of the grey tone, intended to illustrate that a voxel or a pixel represents a part of a vascular structure, as can be detected, for example, on the basis of the image value which lies above or below a given threshold value, it can be recognized that in the difference image $F_1$ a corresponding pixel $P_1$ exists for the voxel $V_1$. This means that the segment of the vascular system represented by the voxel $V_1$ has been filled with contrast medium in the time interval corresponding to the difference image $F_1$. Therefore, the voxel $V_1$ is marked as symbolically indicated by the arrow 22.

The same holds for the voxel $V_2$ which is projected onto the pixel $P_2$ and is also marked. The voxel $V_3$, projected onto the pixel $P_3$, however, is not marked because the pixel $P_3$, or the part of the object to be examined which is represented by this pixel, has not been filled with contrast medium in the difference image $F_1$.

In conformity with this method all voxels $V_k$ of the reconstruction sub-image R', or at least all voxels reproducing the vascular system, are successively compared with the pixels of each individual difference image $F_j$ so as to be marked. In the example shown the voxels $V_1$ and $V_2$, being the only voxels marked after the comparison with the difference image $F_1$, form the voxel sub-set $L_1$ which can be represented by a first color in the three-dimensional reconstruction image formed upon completion of the method. The voxel sub-set $L_1$ thus contains all voxels into which contrast medium has flown in the time interval between the formation of the X-ray projection images $E_0$ and $E_1$.

A reconstruction sub-image R' can also be obtained in a manner other than that described with reference to FIG. 2, for example, by subtraction angiography. To this end, two series of X-ray projection images are formed from different X-ray positions by means of the imaging unit 12, 13, that is, once with and once without administration of contrast medium. The X-ray projection images of the two series that are formed from each time the same X-ray position are then subtracted from one another and the resultant projection images are reconstructed so as to form the desired reconstruction sub-image R'.

FIG. 4 shows the flow chart of a further version of the method according to the invention. This flow chart deviates from that of the version shown in FIG. 2 first of all in that only a single series of X-ray projection images $D_i$ is acquired; no X-ray projection images $E_j$ are acquired from a fixed X-ray position, so that the second imaging unit 12', 13' (see FIG. 1) can also be dispensed with. The steps 200 to 203 otherwise correspond without modification to the steps 100 to 104 with omission of the step 102.

During the subsequent step 204 the X-ray projection images $D_i$ are segmented, that is, the pixels representing the vascular structures in the individual images $D_i$ are selected and reproduced exclusively in the segmented X-ray projection images $D_i'$, while other image elements such as, for example the background or other organs, are eliminated. This operation can be performed, for example, by means of the image values which lie above or below a given limit value for the vessels filled with contrast medium whereas this is usually not the case for other image elements.

The successive segmented X-ray projection images $D_i$ are subsequently individually compared with the reconstruction sub-image R' or the pixels $P_1$ of the segmented X-ray projection images $D_i'$ are compared with the voxels $V_k$ of the reconstruction sub-image R'. This operation takes place in the same way as described with reference to FIG. 3 for the difference images $F_j$. The voxel sub-sets $L_j$ and the images B for reproducing the blood flow are formed in the steps 206 and 207 in the same way as already described above. The method is completed again in the step 208.

In comparison with the version described with reference to FIG. 2 the present version offers the advantages that only one imaging unit (12, 13) is required and that only a single series of X-ray projection images $D_i$ need be acquired. The segmentation of the images $D_i$ in the step 204, however, may be difficult in practice and could give rise to inaccuracies. Moreover, the information contents of the segmented X-ray projection images $D_i'$ differ from that of the difference images $F_j$ which contain the variation of the blood flow as a function of time in a time interval whereas the segmented X-ray projection images $D_i'$ show the entire region of the vascular system filled with the contrast medium.

A third version of the method according to the invention will be described in detail with reference to FIG. 5. After the start in the step 300, a two-dimensional X-ray image data set H is acquired in the step 301. This may be a single X-ray projection image which reproduces the complete vascular system filled with a contrast medium, or an image composed of a plurality of individual X-ray projection images. The data set H may also have been acquired already at an earlier instant. During the step 302 a series of X-ray projection images $E_j$ is acquired (after contrast injection) from a fixed X-ray position by means of the imaging unit (12, 13). At the same time, or subsequently, the two-dimensional image data set H is segmented in the step 303, so that the segmented image data set H' contains only the vessel structures.

In the step 304 respective difference images $F_j$, having the already described information contents are determined from each time two temporally successively acquired X-ray projection images $E_{j-1}$, $E_j$. These difference images $F_j$ are then individually compared successively with the segmented image data set, that is, the pixels $P_1$ of each individual difference image $F_j$ are compared with the pixels $P_k$ of the segmented two-dimensional image data set H'. To this end it is necessary that the X-ray projection images $E_j$ and the two-dimensional image data set have been acquired by means of the same imaging unit and from the same X-ray position. This comparison in the step 305 produces in an associated pixel sub-set $M_j$ for each difference image $F_j$ in the step 306; this pixel sub-set is comparable to the already described voxel sub-sets $L_j$ and contains the information as to which pixels of the segmented image data set H' represent a part of the vascular system which has been filled with contrast medium in a given time interval or wherefrom the contrast medium has been drained during this time interval.

After the steps 305 and 306 have been performed n times, the entire segmented image H' will have been encoded in time and one or more images can be displayed in order to visualize the blood flow in this image as a function of time (step 307), thus terminating the method (step 308).

The described X-ray device and the described versions of the method according to the invention have been given merely by way of example. The X-ray device may also have a different construction. Individual steps of the method, for example the acquisition of X-ray projection images, may be performed in a different manner in practice.

What is claimed is:

1. A method of imaging the blood flow as a function of time in an object (3) to be examined, which method includes the following steps:

a) acquisition of a series of X-ray projection images ($D_i$; $E_j$) during administration of a contrast medium to the blood vessels in the object (3) to be examined, b) acquisition of an image data set (H; K) containing the course of the blood vessels in the object (3) to be examined, c) segmentation of the regions of the blood vessels in the individual X-ray projection images ($D_i$; $E_j$) that are filled with contrast medium, d) encoding the image data set (H; K) in time by comparing the image data set (H; K) with the segmented X-ray projection images ($D_j'$; $F_j$), the image data set (H; K) including an X-ray image data sub-set (H') having pixels (Pk) representative of information concerning the course of blood vessels, from which one or more pixel sub-sets ($M_j$) are acquired; and e) displaying one or more images (B) formed from the time-encoded image data set (H'; R) based on the one or more pixel sub-sets ($M_j$) and representing the blood flow as a function of time.

2. A method as claimed in claim 1, characterized in that the X-ray projection images ($E_j$) are acquired from a fixed X-ray position ($r_4$), that the image data set is a two-dimensional X-ray image data set (H), that respective difference images ($F_j$) are formed from each time two temporally successive X-ray projection images ($E_j$) in order to segment the X-ray projection images ($E_j$), and that the encoding in time is performed by comparing the two-dimensional X-ray image data set (H) with the difference images ($F_j$).

3. A method as claimed in claim 2, characterized in that the pixels ($P_k$) of the X-ray image data sub-set (H') are projected onto the difference images ($F_j$), that associated pixel sub-sets ($M_j$) are acquired for the individual difference images ($F_j$), that those pixels ($P_k$) of the X-ray image data sub-set (H') for which the associated difference image ($F_j$) comprises corresponding pixels ($P_1$) are assigned to a pixel sub-set ($M_j$).

4. A method as claimed in claim 1, characterized in that the X-ray projection images ($D_i$) are acquired from different X-ray positions ($r_1$, r2, $r_3$), and that the image data set is a three-dimensional X-ray image data set (K) derived from said X-ray projection images ($D_i$).

5. A method as claimed in claim 1, characterized in that the X-ray projection images ($E_j$) are acquired from a fixed X-ray position ($r_4$), that a second series of X-ray projection images ($D_i$) is acquired from different X-ray positions ($r_1$, $r_2$, $r_3$), that the image data set is a three-dimensional X-ray image data set (K) derived from the second series of X-ray projection images ($D_i$), and that respective difference images ($F_j$) are derived from each time two temporally successive X-ray projection images ($E_j$) in order to segment the X-ray projection images ($E_j$) of the first series.

6. A method as claimed in claim 4 or 5, characterized in that a three-dimensional reconstruction image (R) is derived from the X-ray image data set (K), that a reconstruction sub-image (R') which contains essentially the blood vessels is derived from the reconstruction image (R), and that the encoding in time of the image data set (K) is performed by comparison of the reconstruction sub-image (R') with the segmented X-ray projection images ($E_j'$; $F_j$).

7. A method as claimed in claim 6, characterized in that the voxels ($V_k$) of the reconstruction sub-image (R) are projected onto the segmented X-ray projection images ($E_j'$; $F_j$) in order to compare the reconstruction sub-image (R') with the segmented X-ray projection images ($E_j'$; $F_j$), that associated voxel sub-sets ($L_j$) are determined for the individual segmented X-ray projection images ($E_j'$; $F_j$), that those voxels ($V_k$) for which the associated X-ray projection image ($E_j'$; $F_j$) contains corresponding pixels ($P_1$) are assigned to a voxel sub-set ($L_j$), and that one or more three-dimensional reconstruction images (B) are formed from the voxel sub-sets ($L_j$).

8. A method as claimed in claim 3 or 7, characterized in that the pixel sub-sets ($P_j$), or the voxel sub-sets ($L_j$), are reproduced in a different color in the projection image (B) or the reconstruction image (B).

9. A method as claimed in claim 3 or 7, characterized in that a respective reconstruction image (B) is formed from each pixel sub-set ($P_j$), or voxel sub-set ($L_j$), and that such reconstruction images (B) are successively displayed in rapid succession.

10. An X-ray device for carrying out the method claimed in claim 1, which device includes:

an imaging unit (1) with an X-ray source (12) and an X-ray detector (13) for the acquisition of a series of X-ray projection images ($D_i'$; $F_j$) during administration of a contrast medium to the blood vessels, and for the acquisition of an image data set (H; K) containing the course of blood vessels in the object (3) to be examined, an arithmetic unit (19) for segmenting the regions of the blood vessels in the individual projection images ($D_i$; $F_j$) that are filled with the contrast medium and for the encoding in time of the image data set (K) by comparison of the image data set (H; K) with the segmented X-ray projection images ($D_j'$; $F_j$), the image data set (H; K) including an X-ray image data sub-set (H') having pixels representative of information concerning distribution of the contrast medium at a given instant from which one or more pixel sub-sets are acquired; and a display device for the display of one or more images (B) that are derived from the time encoded image data set (H'; R') based on the pixel sub-set and represent the blood flow as a function of time.

11. An X-ray device as claimed in claim 10, characterized in that the imaging unit includes a first X-ray source (12) and a first X-ray detector (13) for the acquisition of a first series of two-dimensional X-ray images ($E_j$) from a fixed X-ray position ($r_4$), and also includes a second X-ray source (12) and a second X-ray detector (13') for the acquisition of a second series of two-dimensional X-ray images ($E_j$) from different X-ray positions ($r_1$, $r_2$, $r_3$).

* * * * *